United States Patent [19]
Rydell

[11] Patent Number: 5,282,799
[45] Date of Patent: Feb. 1, 1994

[54] BIPOLAR ELECTROSURGICAL SCALPEL WITH PAIRED LOOP ELECTRODES

[75] Inventor: Mark A. Rydell, Golden Valley, Minn.

[73] Assignee: Everest Medical Corporation, Minneapolis, Minn.

[21] Appl. No.: 728,337

[22] Filed: Jul. 11, 1991

Related U.S. Application Data

[63] Continuation-in-part of Ser. No. 685,045, Apr. 15, 1991, abandoned, which is a continuation-in-part of Ser. No. 645,186, Jan. 23, 1991, abandoned, which is a continuation-in-part of Ser. No. 571,783, Aug. 24, 1990, abandoned.

[51] Int. Cl.$^5$ .............................................. A61B 17/39
[52] U.S. Cl. ........................................ 606/48; 606/50; 606/42; 604/35
[58] Field of Search ................. 606/42, 45, 46, 48-50; 604/35; 219/236, 237

[56] References Cited

U.S. PATENT DOCUMENTS

| | | | |
|---|---|---|---|
| 164,184 | 6/1875 | Kidder | 606/50 |
| 3,807,404 | 4/1974 | Weissman et al. | 606/42 |
| 4,043,342 | 8/1977 | Morrison, Jr. | 606/50 X |
| 4,060,087 | 11/1977 | Hiltebrendt et al. | 606/48 |
| 4,074,718 | 2/1978 | Morrison, Jr. | 606/48 X |
| 4,161,950 | 7/1979 | Doss et al. | |
| 4,248,231 | 2/1981 | Herczog | |
| 4,362,160 | 12/1982 | Hiltebrendt | 606/46 |
| 4,493,320 | 1/1985 | Treat | |
| 4,674,498 | 6/1987 | Stasz et al. | |
| 4,903,696 | 2/1990 | Stasz et al. | |
| 4,936,281 | 6/1990 | Stasz | 606/50 |
| 5,071,419 | 12/1991 | Rydell et al. | 606/50 X |

FOREIGN PATENT DOCUMENTS 782819 11/1980 U.S.S.R. .

Primary Examiner—Lee S. Cohen
Attorney, Agent, or Firm—Haugen and Nikolai

[57] ABSTRACT

A bipolar electrosurgical scalpel comprising a handle having a pair of loop electrodes extending outwardly from the distal end thereof in parallel, spaced relation, such that the spacing defines a dielectric such as an air gap therebetween. When a RF voltage of a predetermined amplitude is applied across the two electrodes and they are drawn across tissue, cutting occurs by virtue of the arc established between the two electrodes. The electrodes may be formed from tungsten wire to withstand high operating temperatures and are sufficiently rigid to withstand the pressure forces encountered during electrosurgery without shorting together across the gap. The electrodes may be formed in various shapes, depending upon the nature of the cutting desired. Possible configurations include open rounded loops, open elongated loops, open triangular-shaped loops, L- or J-shaped hooks. The supporting conductors to which these electrodes are affixed may be straight tubular legs or curved hooks formed from flattened lengths of metal tubing. The loop electrodes may also be ultrasonically vibrated and/or fluid flushed to enhance removal of char and tissue debris during use. To enhance coagulation properties, metal surface electrodes of relatively large area may be embedded in an insulating end cap of the scalpel and the loop cutting electrodes are designed to be retracted therein such that only the surface electrodes are exposed. The instrument is controlled by either a hand switch or a standard surgical foot switch.

5 Claims, 5 Drawing Sheets

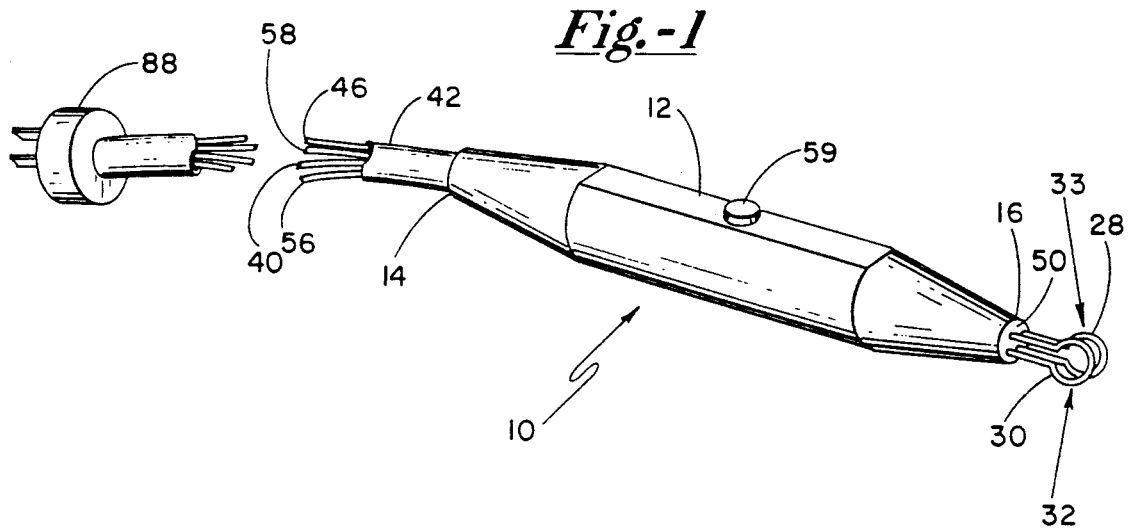
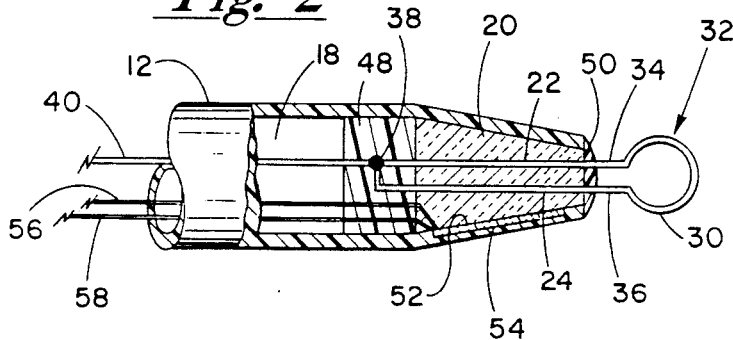
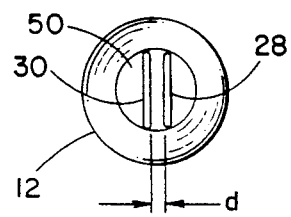
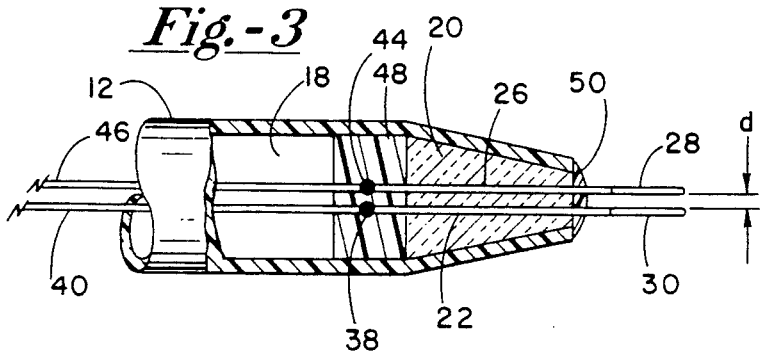

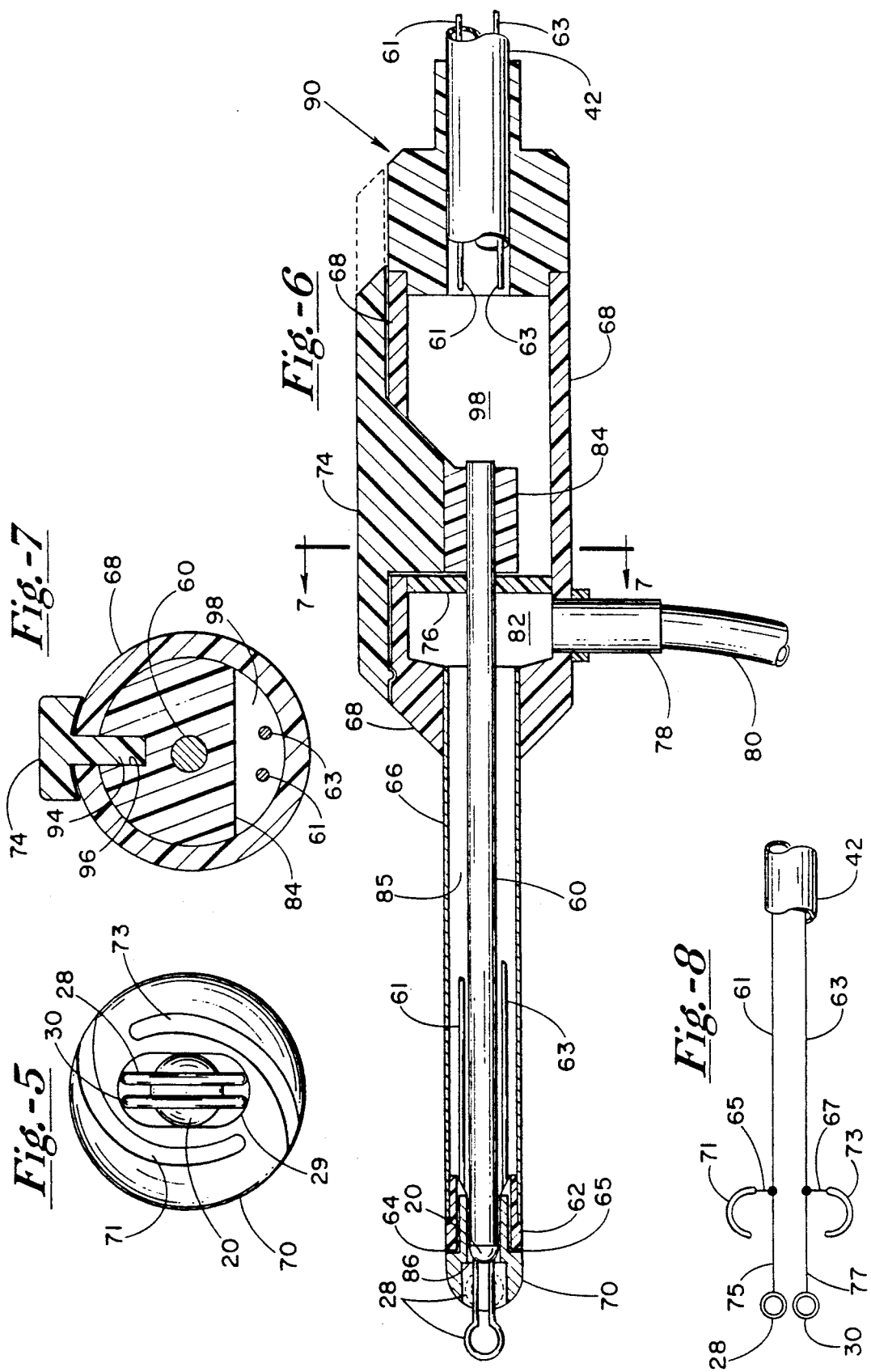

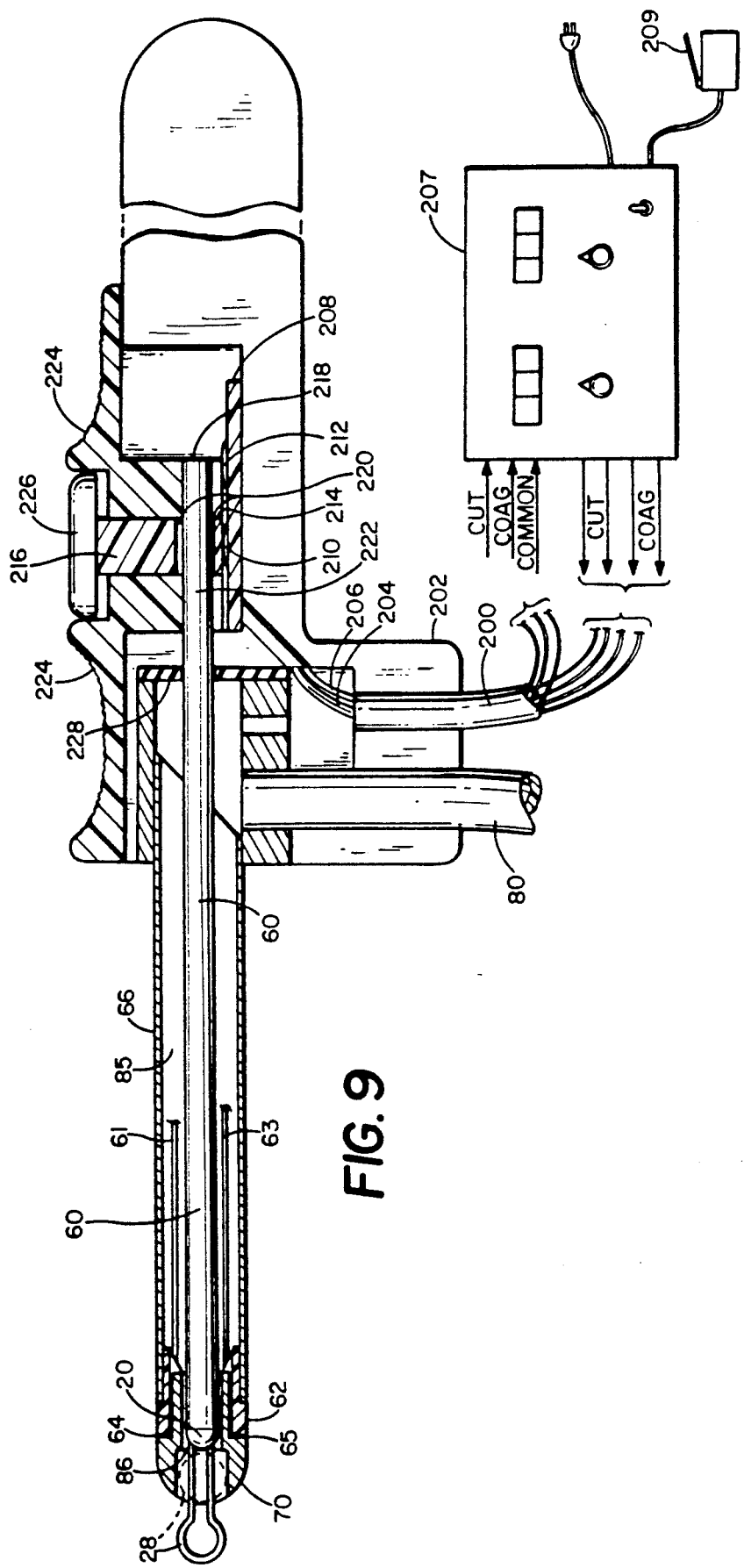

BIPOLAR ELECTROSURGICAL SCALPEL WITH PAIRED LOOP ELECTRODES

CROSS-REFERENCE TO RELATED APPLICATION

This application is a continuation-in-part of application Ser. No. 07/685,045, filed Apr. 15, 1991, now abandoned, which is itself a continuation-in-part of application Ser. No. 07/645,186 filed Jan. 23, 1991, now abandoned, which is itself a continuation-in-part of application Ser. No. 07/571,783, filed Aug. 24, 1990, now abandoned.

BACKGROUND OF THE INVENTION

1. Field of the Invention

This invention relates generally to the design of an electrosurgical scalpel, and more particularly to a bipolar scalpel having specially designed electrodes for facilitating cutting of tissue without the need for an expensive blade of the type heretofore used in prior art bipolar scalpels.

2. Discussion of the Prior Art

In U.S. Pat. No. 4,161,950 to Doss, et al., there is described a knife blade for an electrosurgical scalpel which comprises a thin blade substrate whose periphery is honed to a sharp cutting edge and which carries first and second conductive electrodes adjacent to that cutting edge. The substrate is preferably ceramic and the electrode traces are deposited on the ceramic using known metalizing techniques, wherein a metal powder containing slurry is applied to the substrate through a mask and then later fired to bond the metal to the ceramic substrate. Blades of this type suffer from a number of drawbacks, not the least of which is the cost of producing same. The processing steps involved, including forming the blade substrate, honing its edges, depositing metal conductor traces thereon and subsequently selectively coating the blade surfaces with an insulating material, makes the resulting product relatively expensive, especially, and as will be explained more fully hereinbelow, when contrasted with the present invention.

Blade configurations, such as shown in the Doss '950 patent and in U.S. Pat. No. 4,232,676 to Herzog, suffer from other defects, including breakage and the inability of the electrode foils to withstand the high temperatures resulting when arcing occurs between the active electrode surface and its return electrode.

It is accordingly a principal object of the present invention to provide an improved bipolar electrosurgical scalpel instrument.

Another object is to provide a bipolar electrosurgical scalpel instrument having a low-cost "blade" element which is sufficiently strong to withstand mechanical forces encountered during manufacture, shipping and handling and during use in surgery.

A further object of the invention is to provide a variety of electrosurgical scalpel blade configurations which can withstand elevated temperatures resulting when an arc breakdown occurs between electrodes over prolonged periods of use.

Yet another object of the invention is to provide an electrosurgical instrument having both cutting electrodes and coagulating electrodes where the cutting electrodes are retractable and, when retracted, allow the coagulation electrodes to be used.

Another object is to provide an electrosurgical instrument that can be controlled to operate in either a "cut" mode or a "coag" mode, either by a foot switch or by placement of a thumb-operated switch.

SUMMARY OF THE INVENTION

The foregoing objects and advantages of the invention are achieved by providing an electrosurgical scalpel with a tubular handle having a proximal end and a distal end and with a lumen extending between these two ends. In a first embodiment, two electrodes forming a bipolar pair are mounted on the handle so as to extend longitudinally outward from the distal end of the handle with a dielectric such as an air gap or stabilizing ceramic therebetween. The electrodes themselves each have a generally circular loop shape to them. A pair of wire conductors, insulated from one another, extend through the lumen of the tubular handle and are connected at one end individually to the pair of bipolar electrodes while the other end of the conductors are terminated in a connector for facilitating the coupling of the instrument to an electrosurgical generator.

The loop electrodes are preferably formed from a suitable metal, e.g., tungsten wire, and are rigidly supported in side-by-side relationship in a insulating plug-like insert which fits into the distal end of the tubular handle. Specifically, the insulating insert or plug may have longitudinally extending bores passing therethrough for receiving integrally-formed, closely-spaced, parallel legs which are made to project generally perpendicularly to the circumference of the circular or ellipsoidal loop-shaped electrodes in the same plane as the loop. Electrical connection is then made within the lumen of the tubular handle between the electrical conductors and the leg portions of the pair of bipolar electrodes.

To facilitate self-cleaning of the electrodes during use, and in accordance with the Stasz U.S. Pat. No. 4,674,498, a piezoelectric ultrasonic transducer may be mounted in the handle laterally adjacent to the insulating plug for imparting ultrasonic vibrations thereto when the transducer is driven by an appropriate high frequency alternating current signal.

It is frequently desirable to evacuate or flush the treatment region. To assist in this function, the proximal end of the tubular handle is fitted with a luer lock connector. A fluid delivery or aspiration means may be connected to this luer lock. A port is drilled through the stabilizing insulating tip in the vicinity of the electrodes. Thus, irrigating fluid may be introduced through the luer and travel along the lumen of the tubular handle to exit the port in the insulating tip. Likewise, a suction means may be connected to the luer and the treatment region may be evacuated by withdrawing particles of debris, tissue and fluid through the port, into the handle and out into a collection receptacle joined to the luer.

The loop-shaped electrodes can readily be fabricated from a ductile wire, for example, tungsten alloy. This can be done by appropriate wrapping of the wire about a forming mandrel and because the tungsten alloy wire can be of an appropriate gage to insure rigidity, the blade is very inexpensive to manufacture and holds up well over prolonged periods of use in electrosurgical procedures.

In accordance with a further embodiment, the loop electrodes can be retracted from their normal cutting orientation back into an insulating end cap to thereby allow metal traces disposed on the insulating tip to be exposed to tissue for coagulation.

Yet another embodiment of the present invention features retractable loop electrodes for cutting and an insulating end cap with metal traces for coagulating and which features a handle design with a longitudinally displaceable thumb switch which controls the displacement of the loop electrodes and which provides a lockout, preventing energization of the cut electrodes when the instrument is being used for electrocoagulation. The wiring harness for power and control of the electrosurgical generator employed is routed as a 7-conductor cord exiting alongside an aspirate supply tube.

Still further embodiments feature a pair of closely spaced parallel hook-shaped electrodes. A wire conductor, preferably of tungsten wire, is pressed into various shapes including a pair of elongated loops, a pair of triangular-shaped loops, a pair of J-shaped loops or a pair of L-shaped loops, positioned at various angles relative to the handle and all of which are crimped into curved retainers. A pair of these retainers is rigidly affixed in parallel relationship within an insulating insert or plug positioned at the distal end of the electrosurgical scalpel. As in the nonretractable loop embodiment mentioned above, electrical connection between the electrical conductors and the retainers is made within the lumen of the tubular handle.

DESCRIPTION OF THE DRAWINGS

The foregoing features and advantages of the invention will become apparent to those skilled in the art from the following detailed description of the several embodiments, especially when considered in conjunction with the accompanying drawings in which like numerals in the several views refer to corresponding parts.

FIG. 1 is a perspective view of the electrosurgical instrument in accordance with one embodiment of the present invention;

FIG. 2 is a partial, cross-sectioned side elevational view of the distal end portion of the instrument of FIG. 1;

FIG. 3 is a partial, cross-sectioned top view of the electrosurgicl instrument of FIG. 1;

FIG. 4 is a distal end view of the electrosurgical instrument of FIG. 1;

FIG. 5 is a distal end view of an additional embodiment of the invention;

FIG. 6 is a sectioned side elevation view of the electrosurgical instrument of the alternative embodiment;

FIG. 7 is a cross-sectional view taken along the line 7—7 in FIG. 6;

FIG. 8 is a wiring diagram of the control rod-cutting loop assembly;

FIG. 9 is a sectioned side elevation view of the electrosurgical instrument of yet another alternative embodiment;

DESCRIPTION OF THE PREFERRED EMBODIMENT

Figure 10:
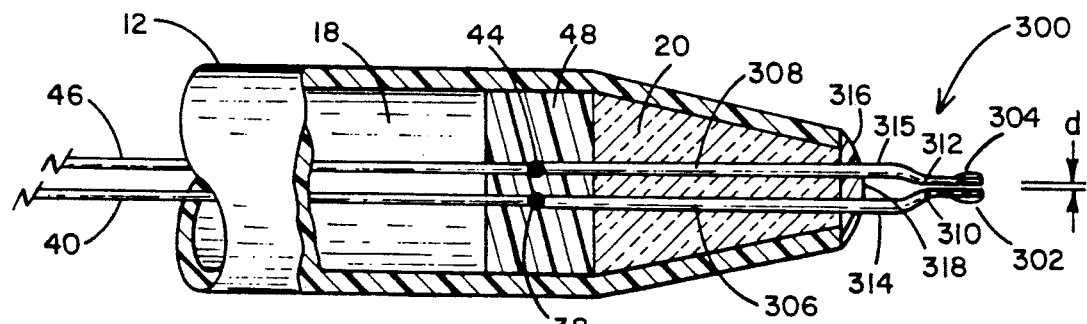
FIG. 10 is a partial, cross-sectioned top elevational view of the distal end portion of yet another embodiment of the present invention featuring elongated looped, hook-shaped electrodes.

Referring to FIG. 1, there is indicated generally by numeral 10 an electrosurgical scalpel constructed in accordance with a first embodiment of the present invention. It is seen to comprise an elongated tubular handle 12, preferably molded from a suitable medical grade plastic, and having a proximal end 14 and a distal end 16 with a lumen 18 (FIG. 2) extending between the two ends. Fitted into the distal end 16 of the tubular handle 12 is an electrode support means in the form of an insulating plug 20. The plug 20 may be formed from a ceramic or high melting point plastic and includes four generally parallel longitudinal bores as at 22 and 24 in FIGS. 2 and 22 and 26 in FIG. 3. Fitted into these bores are first and second electrodes 28 and 30 which form a bipolar pair. These electrodes may be formed from a suitable wire (preferably tungsten alloy) and of a diameter of about 0.010 inch to 0.030 inch, but limitation to that material and dimension is not to be inferred.

As can best be seen in FIG. 2, the wire is bent to form a generally circular or ellipsoidal loop 32 (and 33) with a pair of integrally formed legs 34 and 36 projecting perpendicular to the circumference of the loop and lying in substantially the same plane as the loop. The legs 34 and 36 are dimensioned to fit within the longitudinal bores, as at 22, 24 and 26, and when so inserted, an air gap, d, of approximately 0.010 inch to 0.030 inch (FIGS. 3, 4) separates the two. It is also effective to use an alternative dielectric, such as ceramic, to separate the two loops. Excellent results have been attained when the diameter of the loop portion 32 is approximately 0.125 inch.

The legs 34 and 36 of the first loop electrode 30 are shown as extending beyond the proximal end of the insulating plug 20 and are mechanically and electrically joined together at a junction 38 (FIGS. 2, 3) to a first electrical conductor 40 which extends through the lumen 18 of the handle 12 and forms a part of an electrical cable or cord 42 (FIG. 1) leading to an electrosurgical generator with which the instrument of the present invention is used. Likewise, the legs of the loop-shaped electrode 28 are joined together at a junction point 44 (FIG. 3) and a conductor 46 leads back to the electrosurgical generator through the cord 42 as well. An electrosurgical generator compatible with the scalpel of the present invention is described in the Stasz et al. U.S. Pat. No. 4,903,696.

To provide added rigidity and electrical isolation between the bipolar electrodes 28 and 30, once the insulating plug 20 with the loop electrodes disposed therein is inserted into the distal end 16 of the handle 12, an epoxy potting compound may be injected through the barrel of the handle 12 and is allowed to solidify around the more proximal portions of the loop electrode legs. This epoxy potting is identified by numeral 48 in FIGS. 2 and 3. Alternatively, one skilled in the art will note that the potting 48 may consist of glass frit or other similar material. In a somewhat similar fashion, to maintain the desired dielectric spacing, d, between the aligned loop portions of the electrodes, a bead of epoxy 50 can be placed on the distal end of the plug 20 so as to surround the short leg lengths exiting the distal end of the plug before being bent to form the loops 32, 33 (FIG. 1). In the same manner, enhanced stability can be attained by insertion of a stabilizing plug of ceramic or high melting point plastic between these legs.

As is explained in the Stasz U.S. Pat. No. 4,674,498, when the cutting blade of an electrical scalpel is ultrasonically vibrated as cutting and/or coagulation is taking place, the tendency for burned blood and tissue debris to build up on the blade and to create a short circuit between the bipolar electrodes is significantly reduced. That same concept may be utilized in the electrosurgical scalpel of the present invention by providing a channel 52 (FIG. 2) in the insulating plug 20 and then inserting an ultrasonic transducer 54 into that channel so that it is effectively positioned between the I.D. of the tubular handle 12 and the insulating plug 20. Conductors, as at 56 and 58 (FIG. 2), are joined to the drive electrodes of the ultrasonic transducer 54 and also extend proximally through the handle 12 and through the cord 42 to the electrosurgical generator. When a suitable alternating current drive signal is applied to the transducer, it is made to vibrate in its transverse mode and, in doing so, also vibrates the plug 20 and the electrodes 28 and 30 supported in this insulating plug.

It is often desirable to irrigate and/or aspirate the region surrounding the electrodes. To facilitate these functions, a standard luer lock connector 13 is mounted at the proximal end of tubular handle 12. Tubing (not shown) may be connected to this luer lock and attached to a suction receptacle or a fluid supply. The hollow lumen 18 of the tubular handle 12 may serve as a conduit for the material being flushed or aspirated. An entry/exit port 15 is drilled or otherwise introduced through the plug 20 and epoxy 50 to provide a conduit that will deliver flush fluid in the proximity of the electrodes 28 and 30. One skilled in the art will recognize that a section of tubing (not shown) or similar passage means disposed between luer 13 and irrigation/aspiration port 15 within handle 12 will also serve. In use, a fluid reservoir (not shown) is connected to the luer fitting 13 and fluid is propelled from the reservoir, through the luer fitting 13 and the lumen 18 of the tubular handle 12, through the port 15 and out to the region surrounding the electrodes 28 and 30. When used to aspirate, a source of suction (not shown) is attached to the luer lock 13 and particles of tissue, debris and fluid from the region are withdrawn through port 15 to lumen 18 and luer 13, then out to an aspirate receptacle (not shown).

In use, the surgeon grasps the handle 12 and by appropriate operation of either a handle push button switch 59 (FIG. 1) or a foot switch associated with the generator (not shown), RF power will be applied to the closely spaced loop electrodes 28 and 30. When those electrodes are brought into contact with tissue and drawn in a longitudinal direction, arcing occurs between the two loops which is sufficient to cut through the tissue present in the gap. Because both loops 32 and 33 are identical in size, neither one assumes the role of a conventional return electrode on a permanent basis. Arcing is found to occur from each loop to the other.

The present invention offers the advantage of providing very effective bipolar cutting from an electrode structure that is rugged and relatively easy and inexpensive to fabricate, especially when contrasted to more conventional blades wherein metal traces formed in a mask and etch process or a mask and fire process are adhered to opposed side surfaces of a thin ceramic or metal substrate.

DESCRIPTION OF ALTERNATIVE EMBODIMENTS

FIGS. 5 through 8 depict an alternative embodiment of the present invention which features loop electrodes that are retractable into an insulating end cap and the addition of coagulation electrodes to the surface of the end cap. To enhance the ability to coagulate following cutting, surface electrodes consisting of two spiral strips of metal having an effective surface area much greater than the area of the loop electrodes are concentrically inlaid or otherwise supported on an exterior tip surface of an outer insulating cap member 70 as shown in FIGS. 5 and 6, and described hereinafter.

As with the embodiment of FIGS. 1–4, rounded loop electrodes 28 and 30 are mounted on an insulating tip 20, preferably of ceramic, and stabilized with a resin coating 50 over this insulating tip. These loop electrodes are also comprised of wire, such as tungsten, and dimensioned in the range of about 0.010 inch to 0.030 inch. In contrast to FIG. 1, however, two electrodes labeled 71 and 73 have been deposited on or embedded into the surface of the end cap 70 as two concentric metal helical coils, shown in FIG. 5, each of which terminates alongside the entry/exit bore 29 formed in the end cap 70 which permits passage of the electrodes 28 and 30. The coagulating electrodes are formed from a suitable metal and may be plated or silk-screened onto the end cap to provide the desired spaced-apart geometry. It should be obvious to one skilled in the art that the concentrically inlaid surface electrodes could be of significantly greater width, without impairing the spirit of the present invention. Accordingly, the width of these inlays may be varied, depending upon the desired degree of coagulation, so that they may be narrow or they may approach the shape of half-domes.

In contrast to the embodiment of FIG. 1 where the loop electrodes are immovable, in the alternative arrangement, the tubular handle member 68 incorporates a reciprocally movable control rod 60 surrounded by a tubular control rod housing 66 (FIG. 6). The control rod housing supports the insulating end cap 70 in its distal end and may be held in place by a plastic bushing 62. Gaps 64, 65 of approximately 0.005 inch are provided between the end cap 70 and the plastic bushing 62 to accommodate the routing of fine electrical conductors 65 and 67 (FIG. 8) leading from a proximal connector, through the assembly to coagulator electrodes 71 and 73 whereby an appropriate RF voltage can be established therebetween to effect coagulation.

The control rod housing 66 preferably consists of a Teflon ® coated, stainless steel tubular sleeve and fitted into the distal end thereof is the above-mentioned plastic bushing 62 and the dome-shaped insulating end cap 70. The lumen of housing sleeve 66 may be approximately 0.08 inch diameter and thus allows the control rod 60 to be shifted longitudinally therein. A thumb slide member 74 fitted into a longitudinal slot 96 (FIG. 7) formed in the tubular handle member 68 supports the proximal end portion of the control rod 60. The thumb slide member 74 is affixed to the proximal end of the control rod by means of a guide block 84 in such manner that a length of approximately 0.3 inch of the control rod is embedded into the guide block.

The top of the thumb slide member 74 is angled at its forward end such that it is flush with the distal end of the tubular handle member 68 when the loop electrodes 28 and 30 are exposed for use and its beveled proximal end is flush with the proximal end of the handle member 68 when retracted a distance of approximately 0.5 inch.

To prevent accumulation of coagulated particles, the unit has also been fitted with a flushing mechanism. More particularly, fitted into a well 82 formed in the tubular handle member 68 and surrounding the control rod 60 is a concentric latex seal 76 which prevents back leakage of flushing solution which may be injected into the well 82. The well 82 may be fed by a flushing tube 80 joined to the tubular body by coupler 78. Saline injected through the flushing tube into the well is permitted to flow down the lumen 85 of the control rod housing 66 exiting the annular gap 86 between the exterior of the control rod and the bore in the end cap 70 through which the control rod is designed to slide. Thus, this fluid is prevented from entering the space 98 containing the thumb slide and guide block 84. Following this pathway, saline will serve to flush out any accumulated particles of tissue and blood from the region of the insulating plug, end cap and electrodes.

FIG. 7 is a cross-sectional view taken along the line 7—7 in FIG. 6. The central control rod 60 is embedded in and completely surrounded by a stabilizing guide block 84 which is itself almost completely surrounded by the tubular member 68. The thumb slide member 74 is formed so as to have an extension portion 94 so that it may be mounted atop this tubular member by means of a stabilizing longitudinal guide slot 96. This slot is cut approximately 0.16 inch deep, 0.3 inch long and 0.06 inch wide into the top of the tubular member 68 and guide block 84. It serves to prevent the thumb slide member from shifting sideways as it is pushed proximally or distally. A hollow cavity 98 accommodates wires 61 and 63 leading to the surface coagulating electrodes 71 and 73 embedded in the end cap 70 and for the loop electrodes 28 and 30 mounted on the insulating tip 20.

The proximal end of the unit, which is denoted generally as 90 in FIG. 6, is fitted with a power cord 42 which terminates in a plug 88. The cord is attached to the two circuits 61 and 63 that supply the coagulation and cutting features, as shown in the wiring diagram of FIG. 8. Each separate coagulation/cutting circuit consists of a coagulation surface electrode 71 or 73 wired in parallel with the cutting loop electrodes 28 or 30. The two circuits are wired in series, to the power supply cord 42 utilizing the lumen 85 of the control rod housing 66 and the cavity 98 of the tubular handle member 68. As earlier mentioned, the fine electrical wires 65 and 67 to each of the concentric surface electrodes 71 and 73 is channeled between the insulating end cap 70 and the plastic bushing 62 at 64, 65 of FIG. 6, while the electrical cutting supply wiring 75, 77 protrudes through the insulating tip 20 to the tungsten loop electrodes 28 and 30, as described in the first embodiment.

FIG. 9 shows an alternative handle to be used in conjunction with the retracting loop electrodes and insulating tip combination previously described. This handle differs from the embodiment of FIG. 6 in that FIG. 6 shows a electrosurgical scalpel that is electrically controlled by a foot switch, while FIG. 9 controls the choice of cutting or coagulation functions by placement of a handle-mounted sliding switch.

Referring to FIG. 9, there are shown retractable loop electrodes 28, 30, elongated barrel 66, insulating tip 70, and surface electrodes 71, 73, as in the embodiment of FIG. 6. Furthermore, a flushing and/or aspiration of fluids uses a tube 80 and outlet 86 as in FIG. 6.

The handle is connected to an electrical cable 200 secured in a plastic block 202 which also serves to secure the placement of the flush/aspirate tube 80. Sets of wires 204, 206 coupled to electrosurgical generator 207 supply individual RF cutting or coagulation voltages to the appropriate electrodes when control signals produced by depression of normally-open switches mounted on a printed circuit board 208 are actuated. More specifically, mounted on the upper surface of PC board 208 are a cutting function dome switch 210 and a coagulation function dome switch 212. The contacts of these dome switches are proportioned to mate with the end portion 214 of a push button 216. The control rod 60 extends from the tip portion of the instrument to the push button 216 and the proximal end portion 218 of the control rod 60 extends through a hole 220 bored in the stem 216 of the push button. The control rod is fixed in place with respect to the slide 224 by a set screw 222 and the presence of the control rod distal end in the hole 220 precludes the thumb switch from coming free of the handle. The push button 216 has a thumb tab 226 that sits flush with the upper surface of the slide 224.

The handle is operated in the following manner: When slide 224 is in its most distal position, push button 216 is positioned directly over dome switch 210 and at the same time the loop electrodes 28 are extended. Downward pressure exerted upon thumb tab 226 engages the lower portion 214 of the push button with switch 210, so that electrical power is supplied to the extended loop electrodes 28, 30. When pressure on thumb tab 226 is released, the entire slide 224 may be moved proximally so that eventually the push button is positioned directly over coagulation dome switch 212. The slide 224 is rigidly affixed to the control rod 60 so that proximal movement of the thumb slide 224 retracts the loop electrodes 28, 30 into the insulating tip 70. When the thumb slide 224 is fully proximal, a similar depression of thumb tab 226 and push button 216 closes the dome switch 212 to send a control signal to the electrosurgical generator for applying an appropriate RF signal to the embedded tip electrodes 71, 73 via wires in the cable 200.

A rubber seal 228 encompasses the control rod so that none of the flush fluid supplied by tube 80 may leak into the handle and come in contact with PC board 208.

It is to be understood that electrosurgical generator 207 can be controlled by a standard foot switch 209 as an alternative to the hand switch control described herein.

Referring now to FIG. 10, a still further alternative embodiment 300, which retains the electrocoagulating, flush/aspiration and ultrasonic cleaning capacities of the previously described embodiments, but features hook-shaped electrodes, is shown. Rather than having cutting electrodes formed as rounded loops 28 and 30 mounted on an insulator 20 as in FIG. 3, elongated loops 302 and 304 are formed from conductive material and mounted within curved conductive retainers 306 and 308. The elongated loops 302, 304 are preferably made of tungsten wire or some other appropriate ductile metal, twisted at 180° to double back as shown and spaced approximately 0.010 inch to 0.03 inch apart (d). A suggested size that will optimize cutting capacity yet minimize arcing is about 0.010 inch to 0.030 inch diameter wire. The retainers 306 and 308 are preferably formed of compressible conductive metal tubing. Thus, they may be crimped flat to rigidly secure loops 302 and 304 at junctures 310 and 312. The flattening of these retainer surfaces is desirable because it increases the surface area which enhances bipolar coagulation.

The distal end portions 314 and 315 of these retainers 306 and 308 are rigidly embedded in an insulator, such as ceramic or plastic tip 316. A dielectric gap, d, may be maintained by placing a bead of potting material 318 between the retainers 306 and 308. Additional potting material 48 provides rigidity and electrical isolation at junction points 38 and 44, where the retainers 306, 308 join to the conductive wires 40, 46 within tubular handle 12.

Figure 11:
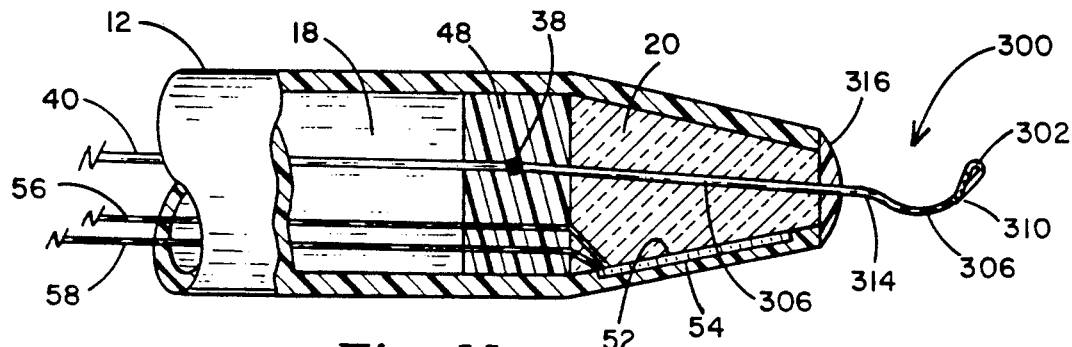
FIG. 11 is a partial, cross-sectioned side view of the distal end portion of the instrument of FIG. 10.

The curvature of the hook-shaped loop electrode configuration 300 is more clearly depicted in FIG. 11. Preferably, the desired degree of curvature is induced in the conductive tubing retainers 306 and 308 before the proximal ends of the loop conductors 302 and 304 are inserted at 310 and 312. The retainer tubing 306 and 308 is then crimped flat to rigidly retain the proximal ends of loops 302 and 304.

Figure 12:
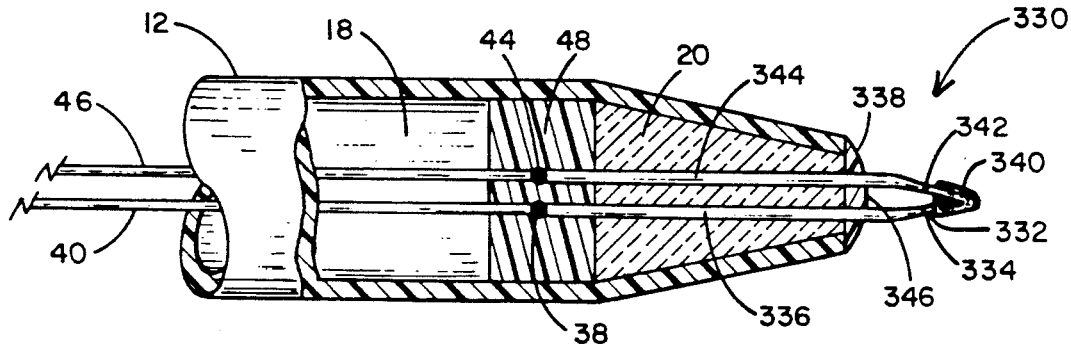
FIG. 12 is a partial, cross-sectioned side elevational view of the distal end portion of an embodiment featuring triangular looped electrodes.
Figure 13:
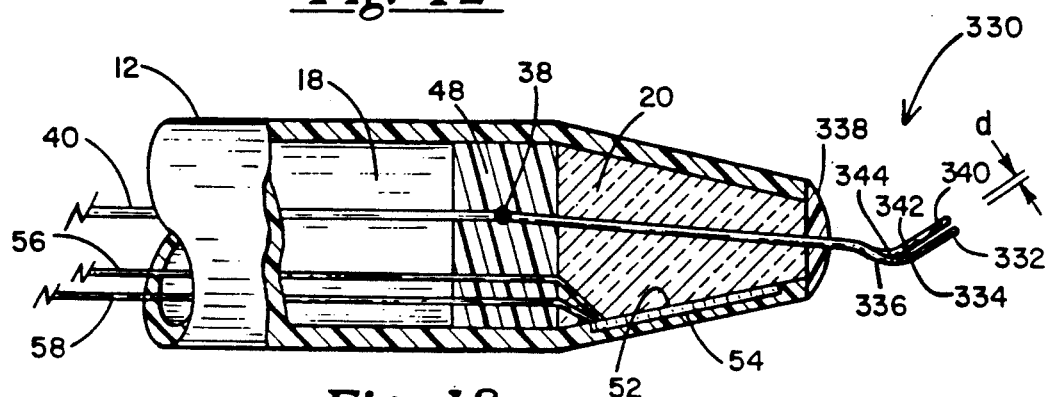
FIG. 13 is a partial, cross-sectioned top view of the distal end portion of the instrument of FIG. 12.

An embodiment featuring cutting electrodes shaped as triangular loops is depicted in FIGS. 12 and 13. The electrocoagulating, flush/aspiration and ultrasonic cleaning capacities of prior embodiments is also retained in this version. The cutting head portion of the instrument is depicted generally at 330, having cutting electrodes 332 and 340 fabricated from conductive metal wire, such as 0.010 inch to 0.030 inch diameter tungsten. As best seen in FIG. 12, they are generally triangular-shaped. Cutting electrode 332 has a leg 334 that is inserted into a section of conductive tubing 336 and held in place by crimping the two together. Similarly, cutting electrode 340 has leg 342 which is inserted and crimped within tubing 344, forming a mirror image of the cutting electrode 332. The conductive electrode tubes 336 and 344 are also preformed so as to be somewhat hook-shaped, as in the embodiment of FIGS. 10 and 11. The tubing 336, 344 is further secured in an end cap 338 with a suitable plastic. The flattened surfaces of the tubes 336 and 344 with dielectric (air) therebetween provides increased surface area, allowing lower current density such that bipolar coagulation can be effected. It is suggested that additional insulating plastic 346 assists in holding the cutting electrodes 332, 340 in a spaced apart relationship of about 0.01 to 0.030 inch (FIG. 13, d). The flattened surfaces of tubes 336 and 344 also extend to junction points 38 and 44, as in previous embodiments, whereupon they are electrically joined to wire conductors 40 and 46 and anchored in insulative potting material 48. As in the embodiment of FIGS. 10 and 11, the flattening of tubes 336 and 344 facilitates bipolar coagulation, while the use of wire for cutting electrodes 332, 340 enhances the cutting of tissue.

Figure 14:
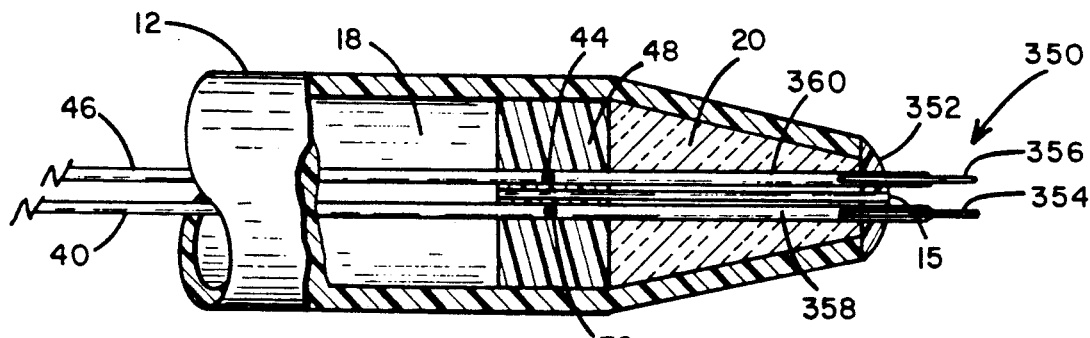
FIG. 14 is a partial, cross sectioned side elevational view of the distal end portion of an embodiment featuring dual-legged, arcuate, looped, hook-shaped electrodes.
Figure 15:
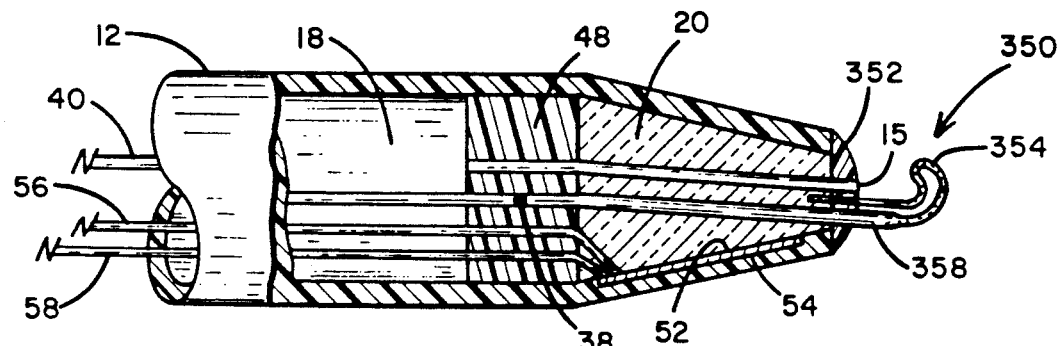
FIG. 15 is a partial, cross-sectioned top view of the distal end portion of the instrument of FIG. 14.

FIGS. 14 and 15 depict an embodiment featuring cutting electrodes shaped as dual-legged, arcuate hooks. Generally depicted as 350, these electrodes are formed from conductive metal wires 354 and 356 which are twisted into a J-shape with a generally hooked end. Material such as 0.010 inch to 0.030 inch diameter tungsten is preferred. Conductive wires 354 and 356 are embedded at their proximal ends into insulation 20 (such as ceramic) and potting material 352. As an in the previous embodiments, conductive tubings 358 and 360 are contoured and dimensioned at their distal ends to be crimped around the distal ends of the wires 354 and 356. The distal ends of the conductive tubings 358 and 360 are also embedded within potting material 352 and insulation 20 at a distance, d, of approximately 0.01 to 0.030 inch and terminate at junction points 38 and 44, as in previous embodiments. At junction points 38 and 44, conductive tubings 358 and 360 are electrically and mechanically joined to conductive wires 40 and 46 and anchored in insulative potting 48. Thus, the particular configuration of these electrodes with the flattened tube surfaces and dielectric (air) therebetween, provide yet another surface upon which to perform by bipolar coagulation. The flattening of the conductive tubings 35 and 360 facilitates bipolar coagulation while the wires 354 and 356 enhance the quality of cutting of tissue. Furthermore, the electrocoagulating, flush/aspiration and ultrasonic cleaning capabilities of prior embodiments are retained.

Figure 16:
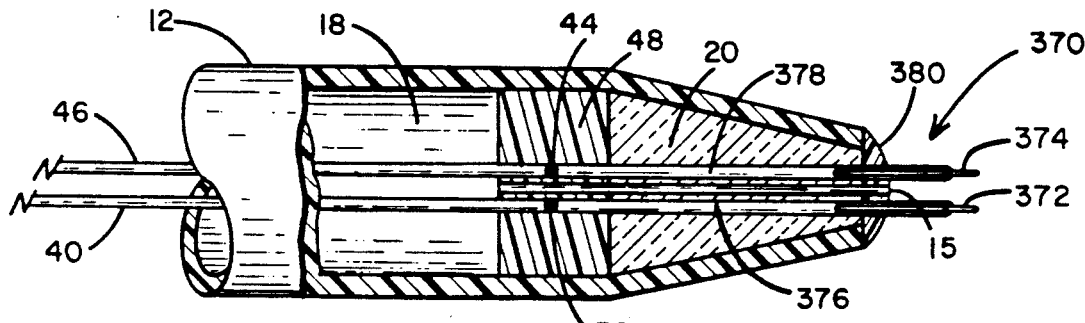
FIG. 16 is a partial, cross sectioned side elevational view of the distal end portion of an embodiment featuring looped, L-shaped electrodes.
Figure 17:
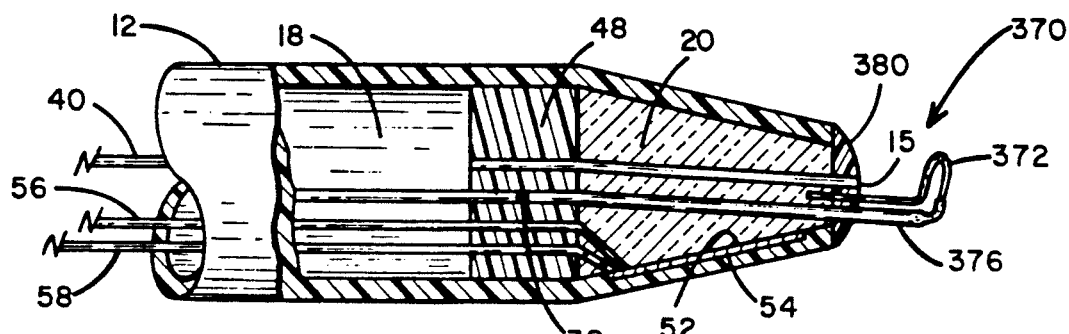
FIG. 17 is a partial, cross-sectioned top view of the distal end portion of the instrument of FIG. 16.

FIGS. 16 and 17 depict yet another embodiment for the cutting electrodes. The electrocoagulating, flush/aspiration and ultrasonic cleaning capabilities of prior embodiments are once again retained, but this embodiment, generally depicted as 370, features electrodes 372 and 374 in an L-shaped configuration. As in the embodiment of FIGS. 14 and 15, these electrodes are formed from material such as conductive wire of approximately 0.010 inch to 0.030 inch diameter wire and are inserted and crimped within conductive retainer tubing 376 and 378. These tubings 376 and 378 are secured at distance, d, of approximately 0.010 inch to 0.030 inch within the tip 370 in potting material 380 and insulation 20. They are also joined to conductive wires 40 and 46 at junction points 38 and 44 and anchored in insulative potting 48. The non-crimped ends of electrode wires 372 and 374 ar embedded within potting 380 and insulation 20 to provide greater stability. Although depicted at an angle of 90° relative to the longitudinal axis of the handle 10 (FIG. 1), one skilled in the art will recognize that these electrodes 372 and 374 may be dimensioned within a range of angles which will all effectuate substantially the same degree of bipolar coagulation in conjunction with the dielectric (air) therebetween. With no limitation intended, examples of such angles are those in the range from 45° through 135°.

The electrodes depicted in FIGS. 14 through 17 are dimensioned to permit the scalpels 350 and 370 to be used as a retractor. When used for this purpose, the free ends of the electrodes are slipped under the organ or tissue to be retracted, then they are withdrawn until these ends hook the tissue and displace it to a desired position which will expose other tissue to be treated. Alternatively, the free ends of these J- and L-shaped electrodes may be used to retract tissue, while simultaneously applying RF voltage to electrocoagulate or cut.

One skilled in the art will recognize that the scalpels depicted in FIGS. 1 through 17 may be dimensioned so that the tubular members 12 and 66 may be passed through a tube or sheath. During procedures such as laparoscopy, this permits electrocoagulation and cutting to be performed with the advantages of the present invention as mentioned heretofore. Also as before, the J- and L-shaped electrodes may be used for retraction and bleeding can be arrested by electrocoagulation, using either the spiral traces 71, 73 on the tip (FIG. 5) or the flattened surfaces of the conductive tubings 336

(FIG. 13), 358 (FIG. 15) and 376 (FIG. 17). When these traces are made to contact small regions of bleeding in vessel walls or seepage from organs, and RF voltage is applied, bleeding will be arrested.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An electrosurgical scalpel comprising:
   (a) a tubular handle having a proximal end, a distal end and a lumen extending therebetween;
   (b) a pair of bipolar electrodes each constructed of a ductile wire of uniform cross-sectional dimension throughout and extending longitudianlly outward from said distal end of said handle with a dielectric therebetween, said electrodes each generally having a closed loop shape; and
   (c) a pair of wire conductors insulated from one another extending through said lumen and connected at one end individually to said pair of bipolar electrodes, the other end including connector means for facilitating connection to an electrosurgical generator.

2. The electrosurgical scalpel as in either claim 1, wherein said pair of bipolar electrodes are formed from wire of tungsten alloy.

3. The electrosurgical scalpel as in either claim 1, wherein said pair of bipolar electrodes are formed from wire of about 0.010 inch to 0.030 inch diameter.

4. The electrosurgical scalpel as in either claim 1, wherein said dielectric is about 0.010 inch to 0.030 inch wide.

5. The electorsurgical scalpel as in either claim 1, wherein said pair of bipolar electrodes are generally circular loop-shaped.

* * * * *

UNITED STATES PATENT AND TRADEMARK OFFICE
CERTIFICATE OF CORRECTION

PATENT NO. :   5,282,799
DATED      :   February 1, 1994
INVENTOR(S) :  Mark A. Rydell It is certified that error appears in the above-indentified patent and that said Letters Patent is hereby corrected as shown below:

Column 12, Line 10, please delete "either".

Column 12, line 13, please delete "either".

Column 12, line 16, please delete "either".

Column 12, line 19, please delete "either".

Signed and Sealed this

Eighteenth Day of October, 1994

Attest:

BRUCE LEHMAN

*Attesting Officer*   *Commissioner of Patents and Trademarks*